(12) United States Patent
Shum et al.

(10) Patent No.: US 9,782,442 B2
(45) Date of Patent: Oct. 10, 2017

(54) CORE-SHELL CAPSULES FOR ENCAPSULATION OF PARTICLES, COLLOIDS, AND CELLS

(71) Applicant: Versitech Limited, Hong Kong OT (HK)

(72) Inventors: Ho Cheung Shum, Hong Kong (CN); Yang Song, Hong Kong (CN)

(73) Assignee: Versitech Limited, Hong Kong (HK)

( * ) Notice: Subject to any disclaimer, the term of this patent is extended or adjusted under 35 U.S.C. 154(b) by 0 days.

(21) Appl. No.: 14/564,372

(22) Filed: Dec. 9, 2014

(65) Prior Publication Data

US 2015/0157576 A1    Jun. 11, 2015

Related U.S. Application Data

(60) Provisional application No. 61/913,660, filed on Dec. 9, 2013.

(51) Int. Cl.
| | |
|---|---|
| *A61K 35/12* | (2015.01) |
| *A61K 35/36* | (2015.01) |
| *A61K 35/33* | (2015.01) |
| *A61K 35/34* | (2015.01) |
| *A61K 35/30* | (2015.01) |
| *A61K 35/22* | (2015.01) |
| *A61K 35/32* | (2015.01) |
| *A61K 9/50* | (2006.01) |

(52) U.S. Cl.
CPC ............ *A61K 35/36* (2013.01); *A61K 9/5031* (2013.01); *A61K 9/5036* (2013.01); *A61K 35/12* (2013.01); *A61K 35/22* (2013.01); *A61K 35/30* (2013.01); *A61K 35/32* (2013.01); *A61K 35/33* (2013.01); *A61K 35/34* (2013.01)

(58) Field of Classification Search
CPC ........... B01L 2300/0645; B01L 3/5027; B01L 9/527; Y10T 428/2989; B05B 5/0255; B05B 5/025; B05B 1/06; B05B 5/087; B05B 7/0408; B05B 5/03; B05B 5/032; B05B 7/066; B05B 12/1472; B05B 7/0846; A61K 35/12; A61K 35/22; A61K 35/30; A61K 35/32; A61K 35/33; A61K 35/34; A61K 35/36; A61K 9/5031; A61K 9/5036

See application file for complete search history.

(56) References Cited

U.S. PATENT DOCUMENTS

2007/0199824 A1* 8/2007 Hoerr ..................... B05B 5/025
                                                           205/80

OTHER PUBLICATIONS

Ziemecka et al. Soft Matter, 2011, 7, 9878-9880.*
Choi et al., J. Controlled Release, 147, 2010, 193-201.*

(Continued)

*Primary Examiner* — Irina S Zemel
(74) *Attorney, Agent, or Firm* — Pabst Patent Group LLP

(57) ABSTRACT

Methods for preparing capsules, such as micro- and/or nanocapsules from all-aqueous emulsions are described herein. The method includes mixing, combining, or contacting a first electrically charged phase containing a first solute with at least an optionally charged second phase containing a second solute. The solutes are incompatible with each other. The electrostatic forces between the two solutions induce the formation of droplets of a dispersed phase in a continuous phase. The droplets are then solidified to form the capsules.

10 Claims, 2 Drawing Sheets

(56) References Cited

OTHER PUBLICATIONS

Andes-Koback and Keating, "Complete budding and asymmetric division of primitive model cells to produce daughter vesicles with different interior and membrane compositions", J. Am. Chem, Soc. 133:9545-9555 (2011).
Balakrishnan, et al., "Particles trapped at the droplet interface in water-in-water emulsions", Langmuir 28:5921-26 (2012).
Boreyko, et al., "Aqueous two-phase microdroplets with reversible phase transitions", Lab Chip 13:1295-1301 (2013).
Bransky, et al., "A microfluidic droplet generator based on a piezoelectric actuator", Lab Chip 9:516-20 (2009).
Brunette and Till, "A rapid method for isolation of L-cell surface membranes using an aqueous two-phase polymer system", J. Membr. Biol., 5:215-24 (1971).
Cans, et al., "Positioning lipid membrane domains in giant vesicles by micro-organization of aqueous cytoplasm mimic", J. Am. Chem. Soc. 130:7400-6 (2008).
Chen, et al., "One-step multicomponent encapsulation by compound-fluidic electrospray", J. Am. Chem. Soc. 130:7800-01 (2008).
Deng, et al., "Increase of electrospray throughput using multiplexed microfabricated sources for the scalable generation of monodisperse droplets", J. Aerosol Sci., 37:696-714 (2006).
Diamond and Hsu, "Aqueous two-phase systems for biomolecule separation", Adv. Biochem. Eng. Biotechnol. 47:89-135 (1992).
Diamond and Hsu, Phase diagrams for dextran-PEG aqueous two-phase systems at 22°C, Biotechnol. Tech., 3:119-24 (1989).
Diamond and Hsu, "Protein partitioning in PEG/dextran aqueous two-phase systems", AIChE J. 36:1017-24 (1990).
Ding, et al., "Interfacial tension in phase-separated gelatin/dextran aqueous mixtures", Colloid Interface Sci.,253:367-76 (2002).
Eggers and Villermaux, "Physics of liquid jets", Rep. Prog. Phys. 71, 036601 (2008).
Forciniti, et al., "Interfacial tension of polyethyleneglycol-dextran-water systems: influence of temperature and polymer molecular weight", J. Biotechnol. 16:279-96 (1990).
Geschiere, et al., "Slow growth of the Rayleigh-Plateau instability in aqueous two phase systems", Biomicrofluidics 6, 022007 (2012).
Giraldo-Zuniga, et al., "Interfacial Tension and Viscosity for Poly-(ethylene glycol) + Maltodextrin Aqueous Two-Phase Systems", J. Chem. Eng. Data 51:1144-7 (2006).
Haas, "Formation of Uniform Liquid-Drops by Application of Vibration to Laminar Jets", Ind. Eng. Chem. Res., 31:959-67 (1992).
Hatti-Kaul, "Aqueous two-phase systems. A general overview", Mol. Biotechnol. 19:269-77 (2001).
Hong, et al., "PEGylated polyethylenimine for in vivo local gene delivery based on lipiodolized emulsion system", J. Controlled Release 99:167-76 (2004).
Jaworek, "Electrostatic micro- and nanoencapsulation and electroemulsification: a brief review", J. Microencapsulation 25:443-68 (2008).
Kaneda, et al.,"Perfluorocarbon nanoemulsions for quantitative molecular imaging and targeted therapeutics", Ann. Biomed. Eng. 37:1922-33 (2009).
Keating, "Aqueous phase separation as a possible route to compartmentalization of biological molecules", Acc. Chem. Res. 45:2114-24 (2012).
Kim, et al., "Multiple polymersomes for programmed release of multiple components", J. Am, Chem. Soc. 133:15165-71 (2011).
King, et al., "Molecular thermodynamics of aqueous two-phase systems for bioseparations", AIChE J. 34:1585-94 (1988).
Lai, et al., "Rounded multi-level microchannels with orifices made in one exposure enable aqueous two-phase system droplet microfluidics", Lab on a Chip, 20:3551 (2011).
Lee, et al., "Microfluidic mixing; a review", Int. J. Mol. Sci., 12:3263-87 (2011).
Lee, et al., "Where physics meets chemistry meets biology for fundamental soft matter research.", Soft Matter 8:3924-3928 (2012).
Li, et al., "Preparation and characterization of crosslinked starch microspheres using a two-stage water-in-water emulsion method", Carbohydr. Polym. 88:912-916 (2012).
Long, et al., "Dynamic microcompartmentation in synthetic cells", PNAS, 102:5920-5925 (2005).
Lorenzen, "Effects of time/temperature-conditions of pre-heating and enzymatic cross-linking on thermo-functional properties of reconstituted dairy ingredients", Food Res. Int., 40:700-8 (2007).
Lu, et al., "Phase separation of parallel laminar flow for aqueous two phase systems in branched microchannel", Microfluid Nanofluid 10:1079-1086 (2011).
Ma, et al., Cell Delivery: Core-Shell Hydrogel Microcapsules for Improved Islets Encapsulation, Adv. Healthcare Mater. 2:768 (2013).
Nguyen, et al., "Stabilization of water-in-water emulsions by addition of protein particles", Langmuir 29:10658-10664 (2013).
Pojman, et al., "Evidence for the existence of an effective interfacial tension between miscible fluids: isobutyric acid-water and 1-butanol-water in a spinning-drop tensiometer.", Langmuir 22:2569-2577 (2006).
Rossow, et al., "Controlled synthesis of cell-laden microgels by radical-free gelation in droplet microfluidics", J. Am. Soc. 134:4983-4989 (2012).
Sauret, et al., "Fluctuation-induced dynamics of multiphase liquid jets with ultra-low interfacial tension", Lab Chip 12:3380-6 (2012b).
Sauret and Shum, "Forced generation of simple and double emulsions in all-aqueous systems", Appl. Phys. Lett. 100:154106 (2012a).
Simeone, et al., "Phase diagram, rheology and interfacial tension of aqueous mixtures of Na-caseinate and Na-alginate", Food Hydrocolloids 18:463-470 (2004).
Simon, et al., "Water-in-water emulsions stabilized by non-amphiphilic interactions: polymer-dispersed lyotropic liquid crystals", Langmuir 23:1453-1458 (2007).
Song, et al., "All-aqueous multiphase microfluidics", Biomicrofluidics,7:061301 (2013b).
Song, et al., "Manipulation of viscous all-aqueous jets by electrical charging", Chem. Commun. 49:1726-1728 (2013a).
Song, et al., "Microextraction in a tetrabutylammonium bromide/ammonium sulfate aqueous two-phase system and electrohydrodynamic generation of a micro-droplet", J. Chromatogr. A 1162:180-186 (2007).
Song and Shum, "Monodisperse w/w/w double emulsion induced by phase separation", Langmuir 28:12054-12059 (2012).
Su and Chiang, "Partitioning and purification of lysozyme from chicken egg white using aqueous two-phase system", Process Biochem. 41:257-263 (2006).
Tang and Gomez, "Generation by electrospray of monodisperse water droplets for targeted drug delivery by inhalation", J. Aerosol Sci. 25:1237-1249 (1994).
Wu, et al., "Fabrication and characterization of monodisperse PLGA-alginate core-shell microspheres with monodisperse size and homogeneous shells for controlled drug release", Acta Blomater. 9:7410-9 (2013).
Wu, et al., "Interfacial Tension of Poly(ethylene glycol) + Salt + Water Systems", J. Chem, Eng. Data 41:1032-1035 (1996).
Zhang, et al., "Polymersomes of asymmetric bilayer membrane formed by phase-guided assembly", J. Controlled Release 147:413-419 (2010).
Zhao, et al., "Plasma lysophosphatidylcholine levels; potential biomarkers for colorectal cancer", Adv. Mater. 19:2696-2701 (2007).
Ziemecka, et al., "Monodisperse hydrogel microspheres by forced droplet formation in aqueous two-phase systems"; Lab Chip, 11:620-4 (2011a).
Ziemecka, et al., "Where physics meets chemistry meets biology for fundamental soft mafter research", Soft Matter 7:9878-9880 (2011b).

(56) References Cited

OTHER PUBLICATIONS

Zoltowski, et al.,"Evidence for the existence of an effective interfacial tension between miscible fluids. 2. Dodecyl acrylate-poly(dodecyl acrylate) in a spinning drop tensiometer", Langmuir, 23:5522-5531 (2007).

* cited by examiner

CORE-SHELL CAPSULES FOR ENCAPSULATION OF PARTICLES, COLLOIDS, AND CELLS

CROSS-REFERENCE TO RELATED APPLICATIONS

This application claims benefit of U.S. Provisional Application No. 61/913,660, filed Dec. 9, 2013. Application No. 61/913,660, filed Dec. 9, 2013, is hereby incorporated herein by reference in its entirety.

FIELD OF THE INVENTION

This invention is in the field of micro- and nanocapsules prepared from all-aqueous emulsions.

BACKGROUND OF THE INVENTION

Hydrogel capsules have been used to encapsulate cells since they can allow facile diffusion of oxygen and nutrients to the cells. Such compositions have been developed as potential therapeutics for a range of diseases including type I diabetes, cancer, and neurodegenerative disorders such as Parkinson's.

Traditional processing of hydrogel particles, such as alginate particles, provides little control over the microstructure or size (diameter) of the capsules. When living cells are encapsulated in the particles, the diffusion of oxygen and nutrients is restricted by the presence of the thick hydrogel shell. Also, proliferation and fusion of cells are prohibited due to the lack of aqueous space.

Moreover, the preparation of such particles often involves the use of organic solvents. Such solvents are costly, toxic, flammable and harmful to the environment. Upon solidifying the dispersed phase to form the solid capsules, organic solvents must be extracted by repeated washing which is time consuming. Therefore, it is highly desirable to replace the organic solvents with all aqueous solute to avoid these tedious steps to remove the organic phases. In addition, when protein solutions are exposed to the oil phase, denaturation of proteins often occurs at the water-oil (w/o) interface, reducing the bioactivity of the proteins.

Recent approaches to produce core-shell hydrogel capsules without the need for organic solvents using miscible aqueous solutions typically resulted in leakage of the payload.

Therefore, there exists a need for improved methods for preparing hydrogel capsules, particularly capsules that prevent leakage of the payload to be encapsulated but allows for efficient passage of oxygen and other nutrients to facilitate cell growth/survival.

SUMMARY OF THE INVENTION

Methods for preparing capsules, such as micro- and/or nanocapsules, from all-aqueous emulsions are described herein. The method includes mixing, combining, or contacting a first electrically charged phase containing a first solute with at least an optionally charged second phase containing a second solute. The solutes are incompatible with each other. The electrostatic forces between the two solutions induce the formation of droplets of a dispersed phase in a continuous phase. The droplets are then solidified to form the capsules.

In some embodiments, a core-shell structured emulsion can also be generated with the all-aqueous electrospray approach. A round capillary with a tapered nozzle can be coaxially inserted into another tapered squared capillary, forming a co-flowing geometry. Two immiscible aqueous phases are separately injected into the inner and outer glass capillaries, forming an inner phase-in-outer phase jet. The outer (shell) phase can be charged by a high-voltage power supply and the compound jet is forced to go through a ring-shaped counter electrode under electrostatic forces. Upon breakup of the jet, core-shell structured droplets finally fall into the continuous phase. The relative sizes of the core and shell of the emulsion can be easily adjusted by changing the flow rates ratios of the two fluids.

The capsules described herein can be used for a variety of applications, such as drug delivery (e.g., small molecules, biomolecules, cells, etc.) and encapsulation of active ingredients, such as proteins, insecticides, herbicides, salts, and macromolecules etc.

DETAILED DESCRIPTION OF THE INVENTION

I. Definitions

Figure 1:
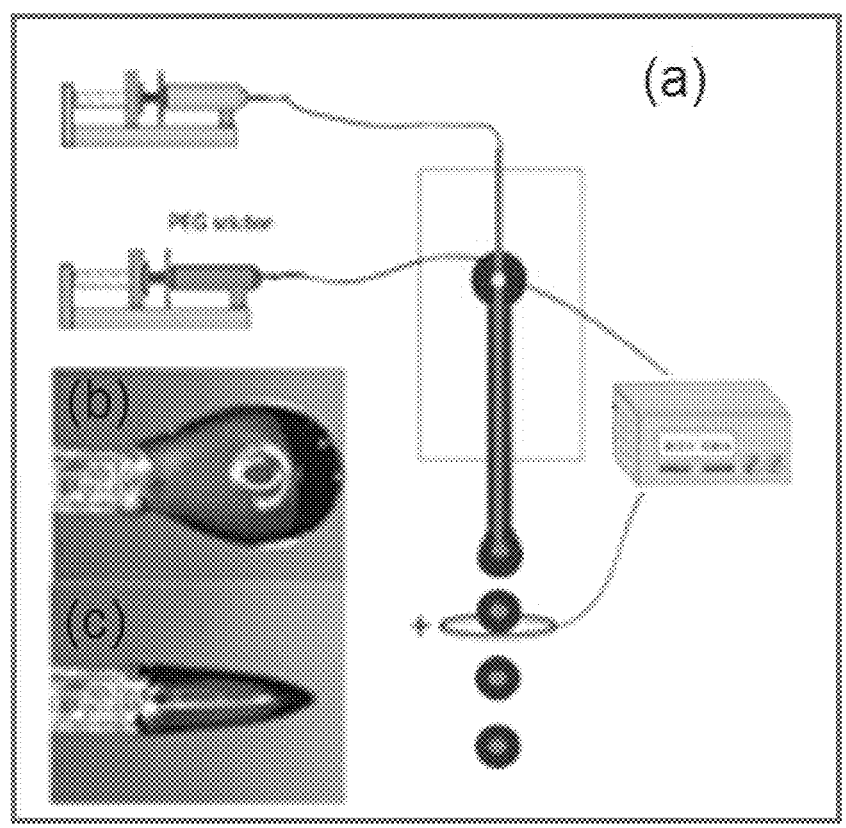
FIG. 1 shows formation of aqueous droplets. Panel a is a schematic of the formation of aqueous droplets in the all-aqueous electrospray approach and the passage of the droplets through a counter electrode. Panel b and panel c are optical images of the coaxial jet/droplets.

"All-aqueous emulsion" and "Aqueous two-phase systems (ATPSs)" are used interchangeable and refer to an emulsion containing an aqueous dispersed phase in an aqueous continuous phase.

"Incompatible", as used herein, generally means the binding energy between two solute molecules of the same kind is lower than the binding energy between two different kinds of solute molecules.

The term "diameter" is art-recognized and is used herein to refer to either of the physical diameter or the hydrodynamic diameter. The diameter of emulsion typically refers to the hydrodynamic diameter. The diameter of the capsules, both in spherical or non-spherical shape, may refer to the physical diameter in the hydrated state. The diameter of the particles, colloids and cells which are encapsulated inside the capsules refers to the physical diameter in the hydrated state. As used herein, the diameter of a non-spherical particle or a non-spherical capsule may refer to the largest linear distance between two points on the surface of the particle. When referring to multiple particles or capsules, the diameter of the particles or the capsules typically refers to the average diameter of the particles or the capsules. Diameter of particles or colloids can be measured using a variety of techniques, including but not limited to the optical or electron microscopy, as well as dynamic light scattering.

The term "biocompatible" as used herein refers to one or more materials that are neither themselves toxic to the host (e.g., an animal or human), nor degrade (if the material degrades) at a rate that produces monomeric or oligomeric subunits or other byproducts at toxic concentrations in the host.

The term "biodegradable" as used herein means that the materials degrades or breaks down into its component subunits, or digestion, e.g., by a biochemical process, of the material into smaller (e.g., non-polymeric) subunits.

The term "microspheres" or "microcapsules" is art-recognized, and includes substantially spherical solid or semi-solid structures, e.g., formed from biocompatible polymers such as subject compositions, having a size ranging from about one or greater up to about 1000 microns. The term "microparticles" is also art-recognized, and includes microspheres and microcapsules, as well as structures that may not be readily placed into either of the above two categories, all with dimensions on average of less than about 1000 microns. A microparticle may be spherical or nonspherical and may have any regular or irregular shape. If the structures are less than about one micron in diameter, then the corresponding art-recognized terms "nanosphere," "nanocapsule," and "nanoparticle" may be utilized. In certain embodiments, the nanospheres, nanocapsules and nanoparticles have an average diameter of about 500 nm, 200 nm, 100 nm, 50 nm, 10 nm, or 1 nm.

A composition containing microparticles or nanoparticles may include particles of a range of particle sizes. In certain embodiments, the particle size distribution may be uniform, e.g., within less than about a 20% standard deviation of the mean volume diameter, and in other embodiments, still more uniform, e.g., within about 10% of the median volume diameter. The term "capsule" as used herein refers to substantially spherical solid or semi-solid structures, e.g., formed from biocompatible polymers such as subject compositions.

The term "particle" as used herein refers to any particle formed of, having attached thereon or thereto, or incorporating a therapeutic, diagnostic or prophylactic agent, optionally including one or more polymers, hydrogel-forming materials, liposomes micelles, or other structural material. A particle may be spherical or nonspherical. A particle may be used, for example, for diagnosing a disease or condition, treating a disease or condition, or preventing a disease or condition. A capsule is a form of particle. Unless the context indicates otherwise, references herein to a particle are understood to include reference to a capsule.

The phrases "parenteral administration" and "administered parenterally" are art-recognized terms, and include modes of administration other than enteral and topical administration, such as injections, and include without limitation intravenous, intramuscular, intrapleural, intravascular, intrapericardial, intraarterial, intrathecal, intracapsular, intraorbital, intracardiac, intradennal, intraperitoneal, transtracheal, subcutaneous, subcuticular, intraarticular, subcapsular, subarachnoid, intraspinal and intrastemal injection and infusion.

The term "surfactant" as used herein refers to an agent that lowers the surface tension of a liquid.

The term "therapeutic agent" refers to an agent that can be administered to prevent or treat a disease or disorder. Examples include, but are not limited to, a nucleic acid, a nucleic acid analog, a small molecule, a peptidomimetic, a protein, peptide, carbohydrate or sugar, lipid, or surfactant, or a combination thereof.

The term "treating" preventing a disease, disorder or condition from occurring in an animal which may be predisposed to the disease, disorder and/or condition but has not yet been diagnosed as having it; inhibiting the disease, disorder or condition, e.g., impeding its progress; and relieving the disease, disorder, or condition, e.g., causing regression of the disease, disorder and/or condition. Treating the disease or condition includes ameliorating at least one symptom of the particular disease or condition, even if the underlying pathophysiology is not affected, such as treating the pain of a subject by administration of an analgesic agent even though such agent does not treat the cause of the pain.

The phrase "pharmaceutically acceptable" refers to compositions, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" refers to pharmaceutically acceptable materials, compositions or vehicles, such as a liquid or solid filler, diluent, solvent or encapsulating material involved in carrying or transporting any subject composition, from one organ, or portion of the body, to another organ, or portion of the body. Each carrier must be "acceptable" in the sense of being compatible with the other ingredients of a subject composition and not injurious to the patient.

The term "pharmaceutically acceptable salts" is art-recognized, and includes relatively non-toxic, inorganic and organic acid addition salts of compounds. Examples of pharmaceutically acceptable salts include those derived from mineral acids, such as hydrochloric acid and sulfuric acid, and those derived from organic acids, such as ethanesulfonic acid, benzenesulfonic acid, and p-toluenesulfonic acid. Examples of suitable inorganic bases for the formation of salts include the hydroxides, carbonates, and bicarbonates of ammonia, sodium, lithium, potassium, calcium, magnesium, aluminum, and zinc. Salts may also be formed with suitable organic bases, including those that are non-toxic and strong enough to form such salts. For purposes of illustration, the class of such organic bases may include mono-, di-, and trialkylamines, such as methylamine, dimethylamine, and triethylamine; mono-, di- or trihydroxyalkylamines such as mono-, di-, and triethanolamine; amino acids, such as arginine and lysine; guanidine; N-methylglucosamine; N-methylglucamine; L-glutamine; N-methylpiperazine; morpholine; ethylenediamine; and N-benzylphenethylamine.

The term "therapeutically effective amount" refers to an amount of the therapeutic agent that, when incorporated into and/or onto particles described herein, produces some desired effect at a reasonable benefit/risk ratio applicable to any medical treatment. The effective amount may vary depending on such factors as the disease or condition being treated, the particular targeted constructs being administered, the size of the subject, or the severity of the disease or condition. One of ordinary skill in the art may empirically determine the effective amount of a particular compound without necessitating undue experimentation. In some embodiments, the term "effective amount" refers to an amount of a therapeutic agent or prophylactic agent to reduce or diminish the symptoms of one or more diseases or disorders of the brain, such as reducing tumor size (e.g., tumor volume) or reducing or diminishing one or more symptoms of a neurological disorder, such as memory or learning deficit, tremors or shakes, etc. In still other embodiments, an "effective amount" refers to the amount of a therapeutic agent necessary to repair damaged neurons and/or induce regeneration of neurons.

The terms "incorporated" and "encapsulated" refers to incorporating, formulating, or otherwise including an active agent into and/or onto a composition that allows for release, such as sustained release, of such agent in the desired application. The terms contemplate any manner by which a therapeutic agent or other material is incorporated into a polymer matrix, including for example: attached to a monomer of such polymer (by covalent, ionic, or other binding interaction), physical admixture, enveloping the agent in a coating layer of polymer, and having such monomer be part of the polymerization to give a polymeric formulation, distributed throughout the polymeric matrix, appended to the surface of the polymeric matrix (by covalent or other binding interactions), encapsulated inside the polymeric matrix, etc. The term "co-incorporation" or "co-encapsulation" refers to the incorporation of a therapeutic agent or other material and at least one other therapeutic agent or other material in a subject composition.

More specifically, the physical form in which any therapeutic agent or other material is encapsulated in polymers may vary with the particular embodiment. For example, a therapeutic agent or other material may be first encapsulated in a microsphere and then combined with the polymer in such a way that at least a portion of the microsphere structure is maintained. Alternatively, a therapeutic agent or other material may be sufficiently immiscible in the polymer that it is dispersed as small droplets, rather than being dissolved, in the polymer.

II. Electrostatic Methods for Producing all Aqueous Emulsions

Methods for preparing all-aqueous emulsions, including stable emulsions and/or emulsions having high viscosity and/or ultra-low interfacial tension are described herein. The method includes mixing, combining, or contacting a first charged solution containing a first solute (e.g., dispersed phase) with an optionally charged second solution containing a second solute (e.g., continuous phase). The solutes are incompatible with each other. It has been discovered that the electrostatic forces between the two solutions induce the formation of droplets of a dispersed phase in a continuous phase.

The emulsions can be used to form micro- and nanocapsules, such as hydrogel capsules. In some embodiments, a coaxial jet is formed by coflowing a first, core phase in a second, shell phase which contains a hydrogel-forming material. The jet is forced through a counter electrode to break up the jet and form core-shell structured droplets. The droplets are solidified to form the capsules by inducing formation of the hydrogel.

A. Incompatible Solutes

Aqueous two-phase systems (ATPSs) are formed by dissolving two incompatible solutes in water above the critical concentrations for phase separation. These incompatible solutes can redistribute in water and form immiscible aqueous phases, if the reduction in enthalpy is sufficient to overcome the energy cost associated with the increased entropy. This often requires each solute species of an ATPS to interact more strongly with itself than with the other species, leading to the segregation of solute of the same species and phase separation.

A variety of solutes known in the art can be used to form the all-aqueous emulsions. Exemplary solutes include, but are not limited to, polymers, such as polyethylene glycol (PEG), dextran, methyl cellulose, polyvinyl alcohol (PVA), and polyvinyl pyrrolidone (PVP), caseinate, and alginate; salts, such as phosphates (e.g., tripotassium phosphate and disodium phosphate), citrates (e.g., sodium citrate), sulfates (e.g., sodium sulfate), and carbonates. In some embodiments, one phase contains PEG and the other phase contains dextran.

The concentration of the solute can vary depending on the nature of the solutes. Generally, the concentration is from about 3.5 wt % to the solubility limited in water. In those embodiments where the solutes are PEG and dextran, the concentration of PEG is from about 3.5 wt % to about 20 wt % and the concentration of dextran is from about 3.5 wt % to the solubility limit of dextran.

The weight average molecular weight of PEG is from about 1,000 Daltons to about 100,000 Daltons, preferably about 2,000 Daltons to about 20,000 Daltons, preferably from about 2,000 Daltons to about 10,000 Daltons, more preferably from about 5,000 Daltons to about 10,000 Daltons. In some embodiments, the molecular weight of PEG is about 8,000 Daltons.

The weight average molecular weight of dextran is from about 40,000 Daltons to about 1,000,000 Daltons, preferably about 70,000 Daltons to about 500,000 Daltons. In some embodiments, the molecular weight is about 500,000 Daltons.

B. Therapeutic, Prophylactic, and Diagnostic Agents

One or more solutions can contain one or more therapeutic, prophylactic, and/or diagnostic agents. In some embodiments, the solution that forms the dispersed phase contains one or more therapeutic, prophylactic, and/or diagnostic agents which are encapsulated within the droplets upon formation of the emulsion. The one or more therapeutic, prophylactic, and/or diagnostic agents can be small molecule therapeutic agents (e.g., agents having molecular weight less than 2000 amu, 1500 amu, 1000, amu, 750 amu, or 500 amu) and/or biomolecules, such as a proteins, nucleic acids (e.g., DNA, RNA, siRNA, etc.), enzymes, etc.

In some embodiments, the agent is a biomolecule, such as a protein, enzyme, nucleic acid, etc. Biomolecules can be denatured in the presence of an organic solvent. Therefore, all aqueous emulsions provide a vehicle for delivering such agents while preserving the biological activity of the agent.

Agents to be delivered include therapeutic, nutritional, diagnostic, and prophylactic compounds. Proteins, peptides, carbohydrates, polysaccharides, nucleic acid molecules, and organic molecules, as well as diagnostic agents, can be delivered. The preferred materials to be incorporated are drugs and imaging agents. Therapeutic agents include antibiotics, antivirals (especially protease inhibitors alone or in combination with nucleosides for treatment of HIV or Hepatitis B or C), anti-parasites (helminths, protozoans), anti-cancer (referred to herein as "chemotherapeutics", including cytotoxic drugs such as doxorubicin, cyclosporine, mitomycin C, cisplatin and carboplatin, BCNU, 5FU, methotrexate, adriamycin, camptothecin, and taxol), antibodies and bioactive fragments thereof (including humanized, single chain, and chimeric antibodies), antigen and vaccine formulations, peptide drugs, anti-inflammatories, nutraceuticals such as vitamins, and oligonucleotide drugs (including DNA, RNAs, antisense, aptamers, ribozymes, external guide sequences for ribonuclease P, and triplex forming agents).

Particularly preferred drugs to be delivered include antiangiogenic agents, antiproliferative and chemotherapeutic agents such as rampamycin.

Exemplary diagnostic materials include paramagnetic molecules, fluorescent compounds, magnetic molecules, and radionuclides.

Peptide, protein, and DNA based vaccines may be used to induce immunity to various diseases or conditions. For example, sexually transmitted diseases and unwanted pregnancy are world-wide problems affecting the health and welfare of women. Effective vaccines to induce specific immunity within the female genital tract could greatly reduce the risk of STDs, while vaccines that provoke anti-sperm antibodies would function as immunocontraceptives. Extensive studies have demonstrated that vaccination at a distal site—orally, nasally, or rectally, for example—can induce mucosal immunity within the female genital tract. Of these options, oral administration has gained the most interest because of its potential for patient compliance, easy administration and suitability for widespread use. Oral vaccination with proteins is possible, but is usually inefficient or requires very high doses. Oral vaccination with DNA, while potentially effective at lower doses, has been ineffective in most cases because 'naked DNA' is susceptible to both the stomach acidity and digestive enzymes in the gastrointestinal tract.

C. Cells

The capsules described herein are prepared from an aqueous dispersed phase and an aqueous continuous phase and therefore do not contain any organic solvents. Such capsules are desirable for encapsulating cells, the viability of which can be adversely affected by the organic solvents. The cells can be added to the phase that becomes the core and/or the phase that becomes the shell.

Exemplary cell types include, but are not limited to, kerotinocytes, fibroblasts, ligament cells, endothelial cells, lung cells, epithelial cells, smooth muscle cells, cardiac muscle cells, skeletal muscle cells, islet cells, nerve cells, hepatocytes, kidney cells, bladder cells, urothelial cells, stem or progenitor cells, neurobalstoma, chondrocytes, skin cells and bone-forming cells.

D. Emulsion Stabilization

Although the all-aqueous emulsions with controlled and tunable structures have been generated with different approaches, all of these emulsions are only transiently stable and tend to coalesce subsequently. Stabilization of these emulsions is thus useful in both scientific studies and practical applications. In preferred embodiments, the emulsions are stabilized by adding a hydrogel-forming material to the shell-forming phase, forming the core-shell droplets, and solidifying the material to form capsules.

1. All-Aqueous Emulsion Templated Materials

Stabilized emulsion structures can be produced by selectively solidifying the dispersed phases, forming hydrogel beads or capsules. To prevent the coalescence of droplets, photo-curable monomers such as PEGDA or dextran-HEMA can be added to the emulsion phase, and the fast photo-polymerization helps to solidify the emulsion within seconds. However, photo-polymerization typically generates toxic free radicals, potentially harming the encapsulated species, especially the living ones. To achieve radical-free gelation, the emulsion phase can be solidified by diffusing biocompatible cross-linkers to the gel precursors in the emulsion phase. For example, when a sodium alginate solution is used as the emulsion phase, the emulsion can be quickly solidified within a minute by introducing calcium ions. Leakage of encapsulated species is negligible within the time scale of emulsion gelation. Nevertheless, many biocompatible gelation reactions, such as enzyme-induced gelation, last for hours to days, where leakage of encapsulated species cannot be disregarded. In this manner, a compact membrane must quickly form at the w/w interface, preventing the leakage of encapsulated species.

Suitable hydrogel forming materials include, but are not limited to, calcium alginate, polymer, such as modified PEGs (e.g., PEG diacrylates), proteins, such as collagen or modified collagen, and block copolymers, such as PLURONICS®. In some embodiments, the hydrogel-forming materials are biocompatible. In other embodiments, the hydrogel-forming materials are biocompatible and biodegradable.

2. Water/Water Interface-Templated Materials

In other embodiments, the emulsion can be stabilized by forming a membrane or barrier on the surface of the dispersed phase droplets to prevent coalescence. Aggregation of particles or macromolecular surfactants at the w/w interface is the primary mechanism of emulsion destabilization. Submicron-sized latex microspheres and protein particles can be irreversibly trapped at the w/w interface. This feature indicates that the absorption energy is larger than the kinetic energy imposed by thermal activation. With a sufficiently large concentration of protein particles and high w/w interfacial tension, protein particles successfully stabilize the PEG/dextran emulsion for a few weeks. However, in the presence of a shear flow, these particles detach from the w/w interface and fail to stabilize the emulsion. Strengthening the binding force among the protein particles may prevent the detachment from the interfaces induced by the shear flow.

Self-assembly of macromolecules at the w/w interface provides another possible solution to stabilize the all-aqueous emulsions. To form stable emulsions, macromolecular surfactants should aggregate at the w/w interface and form a compact membrane. Aggregation of the surfactants at the w/w interface is strongly affected by their interactions with the dissolved solutes in aqueous phases. The presence of such interaction is confirmed by the observation of budding of liposomes encapsulating two immiscible aqueous phases. In this example, two aqueous phases selectively approach the different lipid domains after extraction of water from the liposomes. The interaction between the membrane and the incompatible solutes also keeps the membrane at the w/w interface. This hypothesis is confirmed by using copolymers to form vesicles from the templates of w/w emulsions. In this study, the copolymers of the PEG-polycaprolactone (PCL) and the dextran-PCL are separately added into the PEG-rich and the dextran-rich phase. Upon vortex mixing of the two phases, the two copolymers spontaneously aggregate at the w/w interface. More importantly, the PCL moieties facilitate the formation of a compact membrane, probably due to the hydrophobic interactions.

E. Techniques for Manufacture

Techniques known in the art can be used to prepare the stabilized emulsions described herein. In some embodiments, the emulsion is prepared using an electrospray technique.

Electrospray is a method of generating a very fine liquid aerosol through electrostatic charging. In electrospray, a liquid is passing through a nozzle. The plume of droplets is generated by electrically charging the liquid to a very high voltage. The charged liquid in the nozzle becomes unstable as it is forced to hold more and more charge. Soon the liquid reaches a critical point, at which it can hold no more electrical charge and at the tip of the nozzle it blows apart into a cloud of tiny, highly charged droplets. These tiny droplets are typically less than 10 μm in diameter and fly about searching for a potential surface to land on that is opposite in charge to their own. As the droplets fly about, they rapidly shrink as solvent molecules evaporate from their surface. Since it is difficult for charge to evaporate, the distance between electrical charges in the droplet dramatically decreases. If the droplet can't find a surface in which to dissipate its charge in time, the electrical charge reaches a critical state and the droplet will violently blow apart again.

In the methods described herein, electrospray is used to contact a first aqueous solution containing a first solute and a second aqueous solution containing a second solute, wherein the solutes are incompatible. One of the solutions becomes the dispersed phase in the emulsion while the other becomes the continuous phase. The dispersed and continuous aqueous phase(s) are separated by a middle phase of air, preventing the mixing of charged solutes induced by high voltage. In some embodiments, a dispersed phase (e.g., PEG-containing solution) is charged with a high DC voltage and is sprayed into an immiscible aqueous solution containing the second solute (e.g., dextran) through air. The large surface tension between the dispersed phase and air helps to break up the jet quickly into droplets. A dripping to jetting transition is observed upon an increase in the applied voltage. In the dripping regime, the charged jet immediately breaks up at the end of the spraying nozzle, yielding monodisperse droplets with a polydispersity of less than 5%, 4%, 3%, 2%, or 1%. In the jetting regime, polydisperse droplets are formed at the end of the Taylor cone. A reduction in the size of the spraying nozzle reduces the diameter of the jet, thus facilitating the fast formation of droplets in the electro-dripping regime.

The diameters of the dispersed droplets can be varied as a function of the applied voltage. For example, the diameter of PEG-droplets dispersed in a dextran continuous phase varied from about 800 microns to about 120 microns by increasing the voltage from 4.2 kV to 5.0 kV. At these voltages, the droplets were monodisperse. Polydisperse droplets are obtained with further increases in the applied voltage.

A core-shell structured emulsion can be generated with the all-aqueous electrospray approach. A round capillary with a tapered nozzle can be coaxially inserted into another tapered squared capillary, forming a co-flowing geometry. Two immiscible aqueous phases are separately injected into the inner and outer glass capillaries, forming an inner phase-in-outer phase jet. The outer phase can be charged by a high-voltage power supply and the compound jet is forced to go through a ring-shaped counter electrode under electrostatic forces. Upon breakup of the jet, core-shell structured droplets finally fall into the continuous phase. The relative sizes of the core and shell of the emulsion can be easily adjusted by changing the flow rates ratios of the two fluids. For example, varying the flow rate ratio of the shell (e.g., PEG-rich phase) and core (e.g., dextran-rich phase) from 4:1 to 1:1 to 1:5 resulted in an increase in the size of the core as shown by optical imaging.

A core-shell structured emulsion can also be generated by taking advantage of the phase separation of a single emulsion in an all-aqueous electrospray approach. A single-phase jet containing two or more incompatible solutes breaks up into single emulsion droplets via all-aqueous electrospray. When the single emulsion droplets get into the continuous phase, an osmotic pressure between the two phases drives the condensation of the emulsion phase. This leads to the phase separation of the two incompatible solutes in the droplet. Upon coalescence of the phase separated droplets, the single emulsion droplets are transformed into core-shell structured emulsion droplets.

Core-shell structured capsules can be prepared by using the all-aqueous emulsion as templates. For example, to form hydrogel capsules from the emulsions described herein, a shell phase solution is prepared containing a hydrogel-forming material, such as sodium alginate and a first solute, such as PEG. The core-shell structured droplets are then produced following the same procedure described above by contacting the shell phase solution with second solution (e.g., core solution) containing a second solute which is incompatible with the first solute to form the all aqueous emulsion. In the case of sodium alginate, the droplets are injected into solution containing calcium ions, such as a calcium chloride solution, forming calcium alginate capsules with the identical sizes and geometrical features emulsion droplet template.

To form core-shell structured capsules, solidification of the shell phase can also by achieved by polymerization of the shell phase containing colloids or macromolecular monomers. For example, core-shell structured protein capsules can be formed by dispersing protein-based colloids or monomers into the shell phase as the hydrogel forming materials. Suitable colloids include, but are not limited to, β-lactoglobulin (e.g., diameters ranging from 20 nm to 1000 nm), amyloid fibrils (e.g., length from 30 to 1000 nm), and collagen fiber (e.g Type I collagen from rat tail). Suitable protein-based monomers include, but are not limited to, lysozyme, albumin, insulin, and the like.

In some embodiments, the protein-based colloids and monomers can be initially dispersed in a shell phase solution containing 4 wt % hydroxy-propyl methylcellulose solution. An immiscible aqueous phase, such as 10 wt % dextran, is used as the core liquid phase which forms an emulsion with the hydroxypropyl methylcellulose solution. The core-shell structured droplets are produced following the same procedures described above. The yielded droplets are incubated, for example, at 65-90° C. for more than 24 hours or injected into a sodium chloride solution, forming protein capsules with an aqueous core.

The diameter of the capsules can vary. In some embodiments, the capsules have an average diameter from about 500 nm to about 5 mm, preferably from about 100 microns to about 5 mm. The diameter can be varied by varying the applied electrical field, the diameter of the nozzle, and/or the flow rate.

III. Applications

The micro- and/or nanocapsules described herein can be used for encapsulation applications known in the art, for example, for in vivo drug delivery, encapsulation of active agents for cosmetic applications, encapsulation of insecticides and/or herbicides, etc.

A. Drug Delivery

The emulsions described here can be used to deliver one or more therapeutic, prophylactic, and/or diagnostic agent and/or cells to a patient in need thereof. As discussed above, the emulsions described therein do not contain an organic solvent and therefore are desirable for encapsulating biomolecules (proteins, nucleic acids, etc.) and/or cells, which can be adversely affected by the presence organic solvents. Moreover, the presence of a membrane formed by the oppositely charged macromolecules improves the stability of the emulsions allowing them to be prepared and stored for a period of time before use.

The emulsions can be formulated for a variety of routes of administration. In some embodiments, the emulsion is administered enterally (e.g., oral) or parenterally.

"Parenteral administration", as used herein, means administration by any method other than through the digestive tract or non-invasive topical or regional routes. For example, parenteral administration may include administration to a patient intravenously, intradermally, intraarterially, intraperitoneally, intralesionally, intracranially, intraarticularly, intraprostatically, intrapleurally, intratracheally, intravitreally, intratumorally, intramuscularly, subcutaneously, subconjunctivally, intravesicularly, intrapericardially, intraumbilically, by injection, and by infusion.

The emulsions can be administered neat, i.e., without additional carriers/excipients. Alternatively, the emulsions can be combined with one or more carriers and/or excipients to prepare a pharmaceutical composition.

The carrier can be a solvent or dispersion medium containing, for example, water, ethanol, one or more polyols (e.g., glycerol, propylene glycol, and liquid polyethylene glycol), oils, such as vegetable oils (e.g., peanut oil, corn oil, sesame oil, etc.), and combinations thereof. The proper fluidity can be maintained, for example, by the use of a coating, such as lecithin, by the maintenance of the required particle size in the case of dispersion and/or by the use of surfactants. In many cases, it will be preferable to include isotonic agents, for example, sugars or sodium chloride.

Suitable surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene, and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-β-alanine, sodium N-lauryl-β-iminodipropionate, myristoamphoacetate, lauryl betaine, and lauryl sulfobetaine.

The formulation can contain a preservative to prevent the growth of microorganisms. Suitable preservatives include, but are not limited to, parabens, chlorobutanol, phenol, sorbic acid, and thimerosal. The formulation may also contain an antioxidant to prevent degradation of the active agent(s).

The formulation is typically buffered to a pH of 3-8 for parenteral administration upon reconstitution. Suitable buffers include, but are not limited to, phosphate buffers, acetate buffers, and citrate buffers.

Water soluble polymers are often used in formulations for parenteral administration. Suitable water-soluble polymers include, but are not limited to, polyvinylpyrrolidone, dextran, carboxymethylcellulose, and polyethylene glycol.

Enteral formulations are prepared using pharmaceutically acceptable carriers. As generally used herein "carrier" includes, but is not limited to, diluents, preservatives, binders, lubricants, disintegrators, swelling agents, fillers, stabilizers, and combinations thereof. Polymers used in the dosage form include hydrophobic or hydrophilic polymers and pH dependent or independent polymers. Preferred hydrophobic and hydrophilic polymers include, but are not limited to, hydroxypropyl methylcellulose, hydroxypropyl cellulose, hydroxyethyl cellulose, carboxy methylcellulose, polyethylene glycol, ethylcellulose, microcrystalline cellulose, polyvinyl pyrrolidone, polyvinyl alcohol, polyvinyl acetate, and ion exchange resins.

Carrier also includes all components of the coating composition which may include plasticizers, pigments, colorants, stabilizing agents, and glidants. Formulations can be prepared using one or more pharmaceutically acceptable excipients, including diluents, preservatives, binders, lubricants, disintegrators, swelling agents, fillers, stabilizers, and combinations thereof.

Delayed release dosage formulations can be prepared as described in standard references such as "Pharmaceutical dosage form tablets", eds. Liberman et al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al., (Media, Pa.: Williams and Wilkins, 1995). These references provide information on excipients, materials, equipment and process for preparing tablets and capsules and delayed release dosage forms of tablets, capsules, and granules. These references provide information on carriers, materials, equipment and process for preparing tablets and capsules and delayed release dosage forms of tablets, capsules, and granules.

Stabilizers are used to inhibit or retard drug decomposition reactions which include, by way of example, oxidative reactions. Suitable stabilizers include, but are not limited to, antioxidants, butylated hydroxytoluene (BHT); ascorbic acid, its salts and esters; Vitamin E, tocopherol and its salts; sulfites such as sodium metabisulphite; cysteine and its derivatives; citric acid; propyl gallate, and butylated hydroxyanisole (BHA).

EXAMPLES

Example 1: Preparation of All Aqueous Emulsions Using Electrostatic Effects

Figure 2:
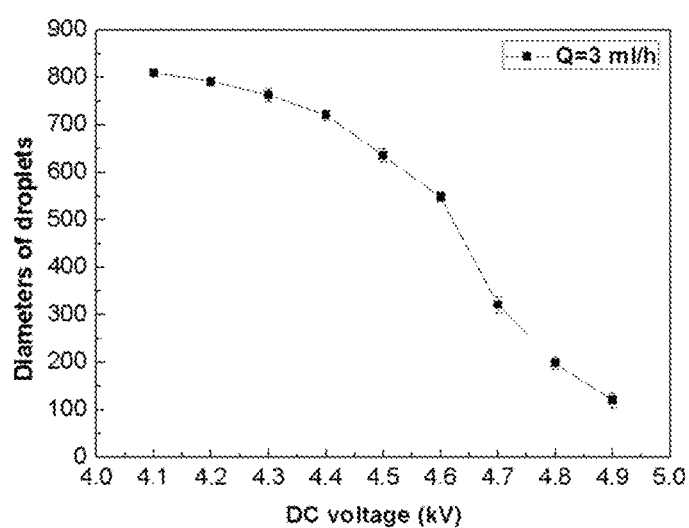
FIG. 2 is a graph showing the diameter of PEG-rich droplets (microns) as a function of the applied DC voltage (kV).

A dispersed phase of 8 wt % PEG (Mw=8,000) solution charged with a high DC voltage is sprayed into its immiscible aqueous phase of 15 wt % dextran (Mw=500,000) solution through air. The large surface tension between the dispersed phase and air helps to break up the jet quickly into droplets (FIG. 1, panel a). A dripping to jetting transition is observed upon an increase in the applied voltage. In the dripping regime, the charged jet immediately breaks up at the end of the spraying nozzle, yielding monodisperse droplets with a polydispersity of less than 5% (FIG. 1, panel b). By increasing the applied electrical field from 2.1 kV/cm to 2.5 kV/cm, the diameter of the produced droplets is significantly reduced from 810 μm to 120 μm (FIG. 2). In this case, the distance between the positively charged nozzle and the negatively charged electrode ring is 2 cm, and the diameter of the nozzle is 40 micrometers. Further increase in the strength of the electric field leads to polydisperse droplets with smaller sizes. A reduction in the size of the spraying nozzle can produce monodisperse droplets with smaller sizes. For example, when the size of nozzle is decreased to 20 μm, uniform droplets with diameters of less than 50 μm are produced.

Example 2: Preparation of Core-Shell All Aqueous Emulsions Using Electrostatic Effects Two immiscible aqueous phases of 10% dextran (Mw=500,000) and 8 wt % PEG (Mw=8,000) solutions were separately injected into inner and outer glass capillaries, forming a dextran-in-PEG jet (FIG. 1, panel a). The PEG-rich phase was charged by a high-voltage power supply and the compound jet was forced to go through a ring-shaped counter electrode under electrostatic forces. Upon breakup of the jet, core-shell structured droplets fell into the continuous phase of a dextran solution or on the surface of a solid substrate (FIG. 1, panel c). The diameter of the core was varied by varying the flow rate ratio of the PEG-rich (shell) and dextran-rich (core) phase. As the ratio was varied from 4:1 to 1:1 to 1:5, the diameter of the core increased.

Core-shell structured capsules can be prepared by using the all-aqueous emulsion as templates. For example, to form calcium alginate hydrogel capsules from the above emulsions, 1 wt %-4 wt % sodium alginate is dissolved into 8% PEG as the shell liquid phase. The core-shell structured droplets are then produced following the same procedures described above. The droplets are injected into 2 wt-8 wt % calcium chloride solutions, forming calcium alginate capsules with the identical sizes and geometrical features to the template of emulsion droplets.

Protein-based colloids and monomers can be initially dispersed in a shell phase solution containing 4 wt % hydroxy-propyl methylcellulose solution. An immiscible aqueous phase, such as 10 wt % dextran, is used as the core liquid phase which forms an emulsion with the hydroxy-propyl methylcellulose solution. The core-shell structured droplets are produced following the same procedures described above. The yielded droplets are incubated, for example, at 65-90° C. for more than 24 hours or injected into a sodium chloride solution, forming protein capsules with an aqueous core.

Figure 3:
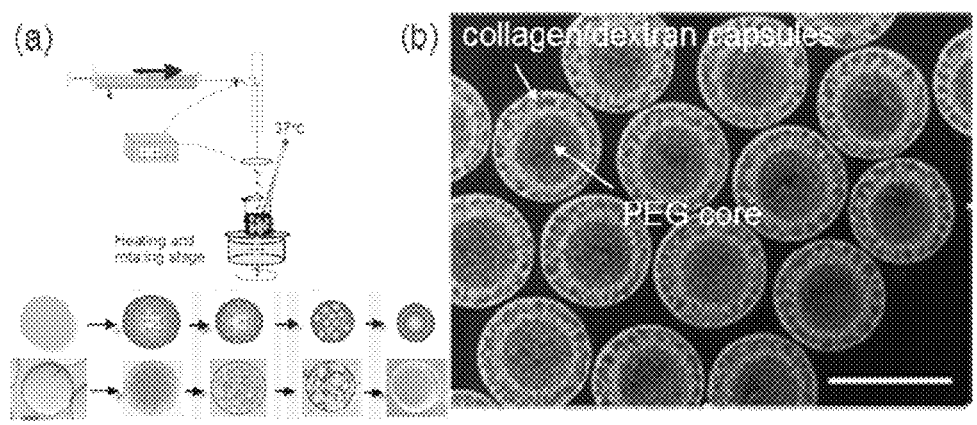
FIG. 3 shows formation of core-shell capsules. Panel a is a schematic of the formation of aqueous droplets and the phase separation of the dextran shell and PEG core. Panel b is a micrograph of PEG/dextran core-shell capsules.

Example 3: Preparation of Core-Shell All Aqueous Emulsions Using Electrostatic Effects A single-phase solution dissolved with 5% dextran (Mw=500,000) and 1% PEG (Mw=20,000) are injected into a glass capillary. This solution was charged by a high-voltage power supply and the compound jet was forced to go through a ring-shaped counter electrode under electrostatic forces. Upon breakup of the jet, single emulsion droplets fell into the continuous phase of 8% PEG (Mw=8,000). Due to osmotic pressure between the two phases, water is gradually extracted from the droplet phase. The condensation of the droplet results in a phase separation inside the droplets, yielding a dextran-rich shell and PEG-rich liquid core (FIG. 3). The diameter of the core was varied by varying the concentration of PEG and dextran in the dispersed phase. As the concentration ratio of dextran and PEG was varied from 4:1 to 10:1, the volume ratio of the shell and core phases decreased accordingly.

Core-shell structured capsules can be prepared by using the all-aqueous emulsion as templates. For example, 1 mg/ml-5 mg/ml collagen, type I is dissolved into the single-phase solution of 5% dextran and 1% PEG. After formation of core-shell structured emulsion, collagen accumulates into the dextran-rich shell. Subsequent solidification of the collagen, either by heating at 37-60° C. for 8-24 hours or chemical cross-linking by 2% glutaraldehyde for 2 hours can lead to the formation of core-shell structured capsules.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A method of making capsules comprising a core and a shell, the method comprising (a) forming a coaxial jet comprising an electrically charged aqueous core phase containing a first solute and an optionally charged aqueous shell phase containing a shell forming material and a second solute which is incompatible with the first solute; (b) breaking up the jet to form core-shell structured droplets; and (c) solidifying the droplets to form the capsules.

2. The method of claim 1, wherein the droplets are formed by forcing the coaxial jet through a counter-electrode.

3. The method of claim 1, wherein the first and second solutes are selected from the group consisting of polyethylene glycol (PEG), dextran, methyl cellulose, polyvinyl alcohol (PVA), polyvinyl pyrrolidone (PVP); tripotassium phosphate, sodium citrate, sodium sulfate, and disodium phosphate.

4. The method of claim 3, wherein the first solute is PEG and the second solute is dextran.

5. The method of claim 4, wherein the molecular weight of PEG is between about 8,000 Daltons and about 20,000 Daltons and the concentration of PEG is 8% and the molecular weight of dextran is about 500,000 Daltons and the concentration of dextran is between about 5% and about 15%.

6. The method of claim 1, wherein the first solution and/or the second solution further contains one or more therapeutic, prophylactic, and/or diagnostic agents that are encapsulated in the droplets.

7. The method of claim 1, wherein the first solution and/or the second solution further contains cells that are encapsulated in the droplets.

8. The method of claim 1, wherein the shell phase further comprises a hydrogel or hydrogel-forming material.

9. The method of claim 8, wherein the hydrogel or hydrogel forming material is sodium alginate.

10. The method of claim 9, wherein the droplet is solidified by the addition of calcium ions.

* * * * *